US00PP37573P2

(12) United States Plant Patent
Schoenmakers

(10) Patent No.: US PP37,573 P2
(45) Date of Patent: Aug. 11, 2026

(54) ***FITTONIA* PLANT NAMED 'KEJAPA124'**

(50) Latin Name: *Fittonia albivenis*
Varietal Denomination: KEJAPA124

(71) Applicant: Schoenmakers Tussenholding B.V., Haaren (NL)

(72) Inventor: Jan Cornelis Adrianus Maria Schoenmakers, Haaren (NL)

(73) Assignee: Schoenmakers Tussenholding B.V., Haaren (NL)

( * ) Notice: Subject to any disclaimer, the term of this patent is extended or adjusted under 35 U.S.C. 154(b) by 0 days.

(21) Appl. No.: 19/392,796

(22) Filed: Nov. 18, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP17,274 P2 * 12/2006 Schoenmakers ..... A01H 6/00 Plt./373

* cited by examiner

*Primary Examiner* — Karen M Redden
(74) *Attorney, Agent, or Firm* — Samuel R. McCoy, Jr.

(57) ABSTRACT

'KEJAPA124' is a new and distinctive *Fittonia* plant which is characterized by a compact, creeping growth habit, broadly lanceolate laminas with sinuate and deeply undulated margins, and dark green laminas with very light green-white bordering the green-white veins which creates a light-lime-green-on-dark-green pinnate variegation pattern. 'KEJAPA124' shows the stability of all these characteristics from generation to generation.

2 Drawing Sheets

Latin name of the genus and species: The Latin name for the genus and species of the novel variety disclosed herein is *Fittonia albivenis*.

Variety denomination: The inventive variety of *Fittonia* disclosed herein has been given the denomination 'KEJAPA124'.

BACKGROUND OF THE INVENTION

Parentage: The claimed plant 'KEJAPA124' originated as a naturally occurring partial-plant mutation of *Fittonia albivenis* 'KEJAPA122' (U.S. patent application Ser. No. 19/375,831). In September of 2010, the inventor discovered the mutation, with its unique light-lime-green-on-dark-green pinnate foliar variegation pattern, growing amongst a cultivated population of 'KEJAPA122' plants in a commercial greenhouse in Haaren, The Netherlands. The mutation was harvested from the parent plant and subsequently propagated by rooting stem cuttings. The resulting plants were then grown to a mature size in order to evaluate and confirm the uniformity and stability of the unique characteristics first observed. Upon confirmation, in September 2011, the inventor selected the claimed *Fittonia* plant 'KEJAPA124' for commercialization due to its unique foliage coloration that differs significantly from the parent plant.

Asexual Reproduction: Asexual reproduction of 'KEJAPA124' by way of rooting stem cuttings, was first performed in September of 2010 at a commercial greenhouse in Haaren, The Netherlands. Through twenty-two subsequent generations, the plants so produced have shown that the unique features of the instant cultivar are stable and reproduced true to type.

SUMMARY OF THE INVENTION

The cultivar 'KEJAPA124' has not been observed under all possible environmental conditions, and the phenotype may vary somewhat with variations in the instant environment such as temperature, day length, and light intensity, without, however, any variance in genotype. The following characteristics have been repeatedly observed and represent the distinguishing characteristics of the new *Fittonia* cultivar 'KEJAPA124'. These traits, in combination, distinguish 'KEJAPA124' as a new and distinct cultivar.

1. *Fittonia* 'KEJAPA124' exhibits a compact, creeping growth habit with decumbent lateral branches that become stoloniferous as the plant matures; and
2. *Fittonia* 'KEJAPA124' exhibits broadly lanceolate laminas with sinuate, deeply undulated margins; and
3. *Fittonia* 'KEJAPA124' exhibits pinnate foliar venation, with very light green-white veins on the adaxial surface, and yellow-green veins on the abaxial surface; and
4. *Fittonia* 'KEJAPA124' exhibits a dark green to yellow-green adaxial foliar surface with green-white, generally appearing as a very light lime green coloration, bordering the network of veins thus creating a strongly contrasting light-lime-green-on-dark-green pinnate variegation pattern.

BRIEF DESCRIPTION OF THE FIGURES

The following photographs were taken using conventional techniques and although colors may appear different from actual colors due to light reflectance, it is as accurate as possible by conventional photographic techniques.

BOTANICAL DESCRIPTION OF THE PLANT

Figure 1:
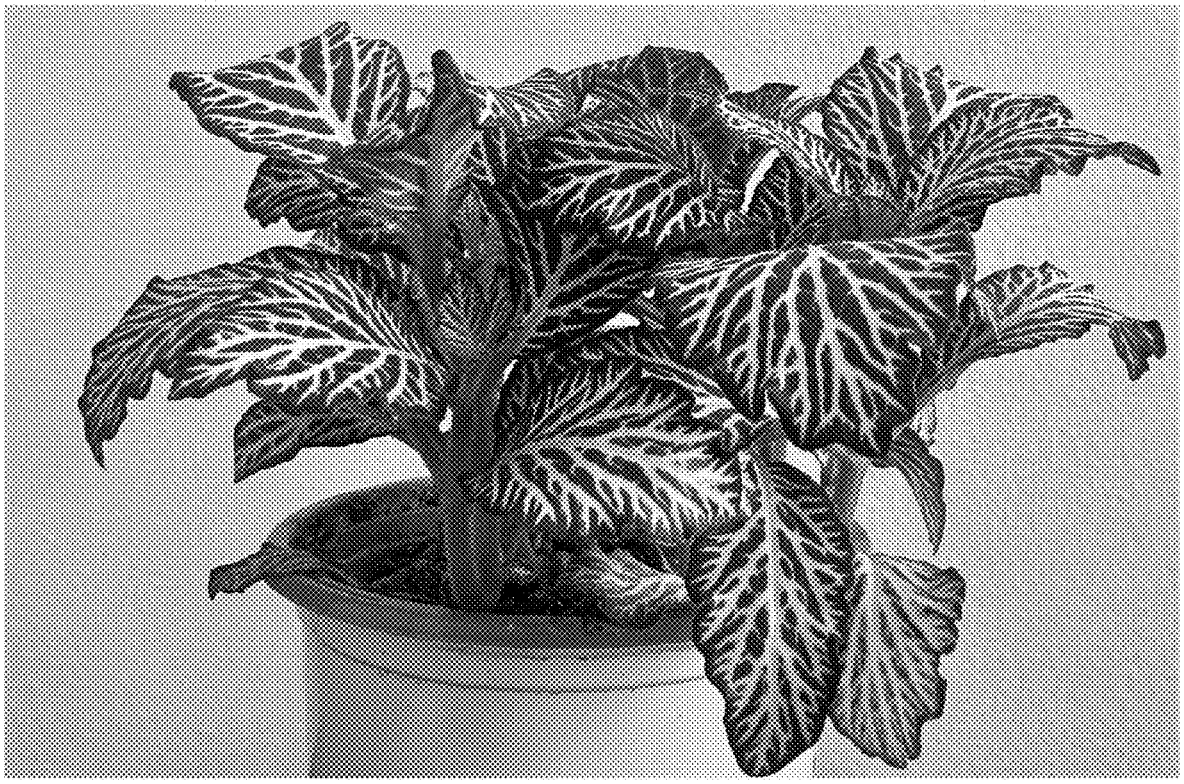
FIG. 1 shows, as nearly true as it is reasonably possible to make the same in color illustrations of this type, an exemplary plant of the new cultivar, 'KEJAPA124', approximately 15-week-old in a 350 mL nursery container. The plant shown was grown from a rooted cutting, potted into a nursery container, grown in a greenhouse in Stuarts Draft, Virginia.
Figure 2:
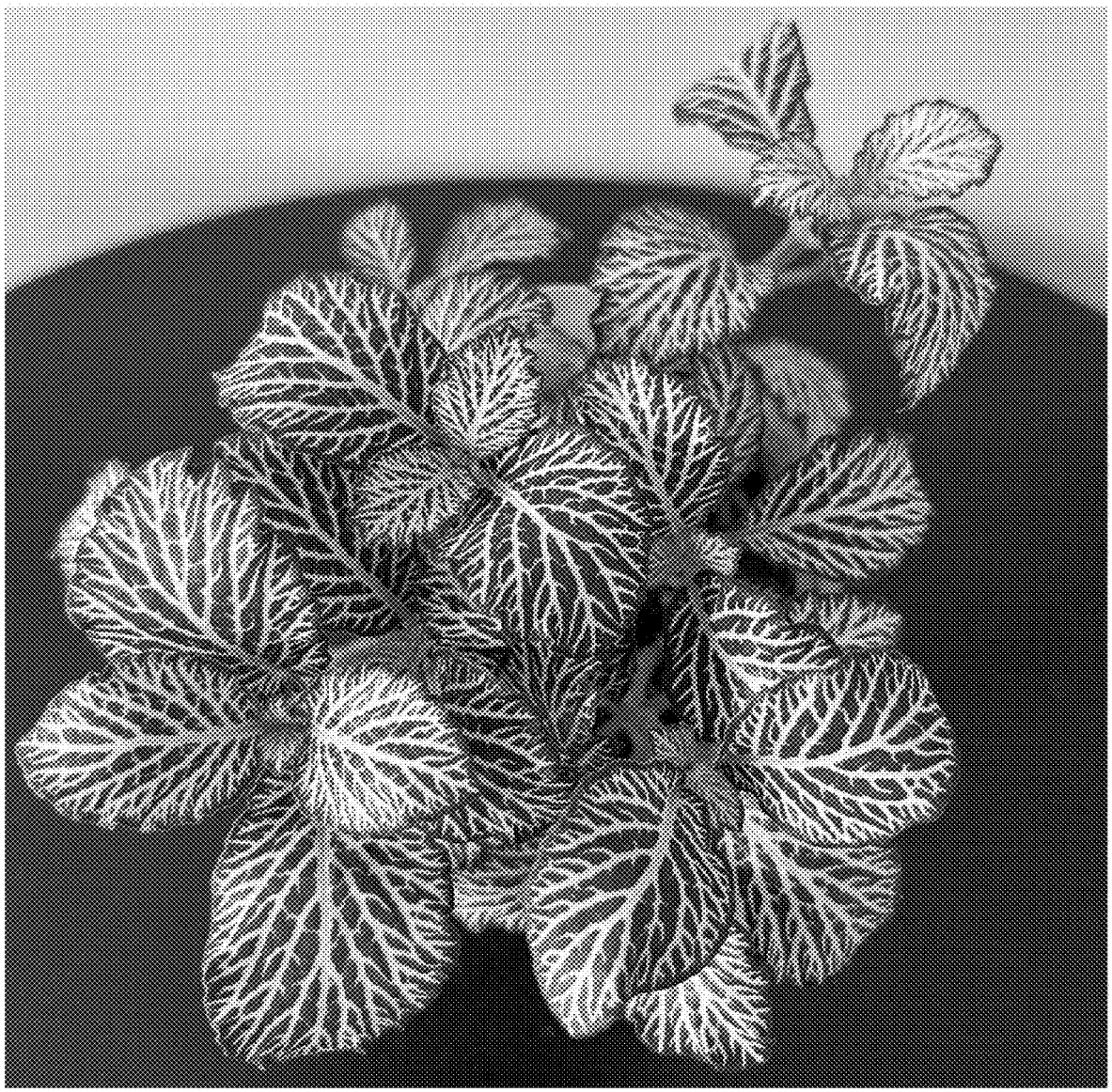
FIG. 2 illustrates the adaxial surface of the juvenile and mature foliage of 'KEJAPA124'.

The following observations and measurements were made in September of 2025. With the exception of the 51-week-old plants used to describe the stoloniferous habit of the plant, the *Fittonia* 'KEJAPA124' plants described in this botanical description are approximately 13-week-old grown in a 350 mL nursery container. Plants were produced using conventional greenhouse production protocols for *Fittonia* species which consisted of overhead irrigation once a week, grown under shade with light levels ranging from approximately 2,000 to 4,000 lumens, with ambient temperatures ranging from 20 to 35 degrees Celsius and humidity levels ranging from 60 to 95 percent. No pest or disease measures were employed. The 51-week-old plants were grown in the same manner as the aforementioned 13-week-old plants, only they were moved to an outdoor area with rain exclusion and 30 percent shade at 30-weeks-old. These plants were manually watered as needed, and no pest or disease control measures were employed.

A botanical description of 'KEJAPA124' and comparisons with the parent plant and the most similar variety of common knowledge are provided below.

Plant description:

*Growth habit*.—Compact, creeping perennial.

*Height*.—10.4 cm.

*Width*.—18.2 cm.

*Propagation*.—Type — Asexual propagation is accomplished by way of rooting stem cuttings. Time to produce a rooted cutting — Approximately 4 weeks to produce a rooted cutting. Time to produce a rooted mature plant — Approximately 14 to 20 weeks grown in a 350 mL nursery container.

*Disease resistance*.—'KEJAPA124' exhibits susceptibility in common with the parent including bacterial leaf spot caused by *Xanthomonas campestris*, fungal blight caused by *Rhizoctonia solani*, as well as common arthropod pests such as aphids, moths, fungus gnats, and thrips.

*Environmental tolerances*.—Adapt to temperatures as high as 31 degrees Celsius. Thrives in partial shade with 60-70% humidity. Leaf scorch will occur in direct sunlight. 'KEJAPA124' requires irrigation once every 5-7 days and prefers growing under 50 $\mu mol/m^2/s$ shaded light.

Root system:

*General*.—Shallow, fibrous root system; stoloniferous.

*Texture*.—Smooth and glabrous.

*Color*.—Greyed-orange, nearest to RHS 165D.

Stem:

*General branching habit*.—Basally branching main stems; with decumbent lateral branches, or stolons, that root at the nodes when in contact with the soil.

*Texture*.—Coriaceous; white, closest to 155A, trichomes present; approximately 0.7 mm in length.

*Luster*.—Glossy.

*Main stems*.—Length — 2.4 cm. Diameter — 0.2 cm. Internode length — 0.3 cm. Attitude — Upright. Texture — Coriaceous and pubescent, with white trichomes present, closest to RHS 155A; trichomes are approximately 0.7 mm in length. Color of developing stems — Green, closest to a blend of RHS 143C and 143D. Color of mature stems — Green to yellow-green, closest to a combination of RHS 143B, 143C, and 144B.

*Stolons*.—Length — 4.8 cm. Diameter — 0.2 cm. Internode length — 0.4 cm. Attitude — Laterally growing from the base of the plant. Cross-section — Terete. Texture — Coriaceous and pubescent, with white trichomes present, closest to RHS 155A; trichomes are approximately 0.7 mm in length. Color — Green, closest to a blend of RHS 143C and 143D. Color at internodes — Yellow-green, closest to RHS 144C.

Foliage:

*Quantity*.—8 leaves per lateral branch.

*Arrangement*.—Opposite.

*Attachment*.—Petiolate.

*Division*.—Simple.

*Lamina*.—Shape — Broadly lanceolate. Length — 4.5 cm. Width — 2.0 cm. Apex — Acute. Base — Acute. Cross-section — Convex. Attitude — Semi-upright. Margin — Sinuate, deeply undulated. Texture and luster of the adaxial surface — Coriaceous and matte. Texture and luster of the abaxial surface — Coriaceous and matte with salient veins. Color — Juvenile foliage, adaxial surface — Yellow-green and green, nearest to a blend of RHS 144C, 137A, and 139A; midrib and lateral veins are margined sharply with green-white, nearest to RHS 157C. This margining of the venation creates a strongly contrasting light lime-on-dark-green, pinnate variegation pattern. Juvenile foliage, abaxial surface — Yellow-green, nearest to a blend of RHS 144A and 144B. Mature foliage, adaxial surface — Yellow-green and green, nearest to a blend of RHS 144C, 137A, and 139A, with the midrib and lateral veins margined sharply with green-white, nearest to RHS 157C. This margining of the venation creates a strongly contrasting light-lime-on-dark-green pinnate variegation pattern. Differing from the juvenile laminas, some mature laminas will have a broader border of green-white to yellow-green, in a blend of RHS 157C and 144C, along the midrib and lateral venation and opaque green, nearest to a combination of RHS 137A and 139A, irregularly outlining the margins. Mature foliage, abaxial surface — Yellow-green, nearest to a blend of RHS 144A and 144B. Venation — Pattern — Pinnate. Color — Juvenile foliage, adaxial surface — Green-white, nearest to RHS 157C. Juvenile foliage, abaxial surface — Yellow-green, nearest to RHS 145D. Mature foliage, adaxial surface — Green-white, nearest to RHS 157C. Mature foliage, abaxial surface — Yellow-green, nearest to RHS 145D.

*Petiole*.—Length — 1.0 cm. Diameter — 0.1 cm. Texture — Coriaceous; trichomes present. Trichomes are white, RHS 155A, and approximately 0.1 cm in length. Luster — Glossy. Color, adaxial surface — Green, closest to a blend of RHS 143C and 143D. Color, abaxial surface — Green, closest to a blend of RHS 143C and 143D.

Inflorescence: No flowering has been observed to date.

COMPARISONS WITH THE PARENT PLANT

Plants of the new cultivar 'KEJAPA124' may be distinguished from the parent plant, *Fittonia albivenis* 'KEJAPA122' (U.S. patent application Ser. No. 19/375,831), by the characteristics described in Table 1.

TABLE 1

Comparison between 'KEJAPA124' and 'KEJAPA122'.

| Characteristic | 'KEJAPA124' | 'KEJAPA122' |
|---|---|---|
| Leaf shape. | Acute to broadly lanceolate with acute apices and bases. | Narrow ovate to lanceolate leaves with narrow apiculate to aristate apices and acute bases. |
| Leaf margins. | Sinuate, deeply undulated. | Serrulate, highly undulated. |
| General coloration of the adaxial surface of mature foliage. | Dark green to yellow-green, with the entire network of venation broadly margined with green-white, which creates a strongly contrasting light lime-green-on-dark-green, pinnate variegation pattern. | Dark yellow-green with a red-purple coloration broadly bordering the entire network of veins which creates a bright-red-on-dark-green, webbed variegation pattern. |
| Venation color, adaxial surface. | Green-white, appearing as a light lime green color. | Red, becoming red-purple as the foliage matures. |

COMPARISONS WITH THE MOST SIMILAR COMMERCIAL VARIETY

Plants of the new cultivar 'KEJAPA124' may be distinguished from the most similar commercial comparator known to the inventor, *Fittonia albivenis* 'KEJAPA123' (U.S. patent application Ser. No. 19/372,654), by the characteristics described in Table 2.

TABLE 2

Comparison between 'KEJAPA124' and 'KEJAPA123'

| Characteristic | 'KEJAPA124' | 'KEJAPA123' |
|---|---|---|
| Leaf shape and size. | Acute to broadly lanceolate with acute apices and bases. On average, 4.5 cm in length. | Lanceolate leaves with acute apices and bases. On average, 2.9 cm in length. |
| Margins. | Sinuate, deeply undulated. | Entire and highly undulated. |
| Expression of variegation on the mature adaxial laminar surface. | Dark green to yellow-green, with the entire network of venation broadly margined with green-white, which creates a strongly contrasting light lime-on-dark-green, pinnate variegation pattern. | Dark green, with the entire cross-venulate network of veins broadly margined with green-white, which creates a dark green and white tessellate variegation pattern. |

That which is claimed is:

1. A new and distinct variety of *Fittonia* plant named 'KEJAPA124', substantially as described and illustrated herein.

* * * * *